(12) United States Patent
Wiechmann (10) Patent No.: US 10,231,800 B2
(45) Date of Patent: Mar. 19, 2019

(54) METHOD FOR PRODUCING A PATIENT-SPECIFIC REPLACEMENT BRACKET FOR AN ORTHODONTIC TREATMENT, AND BRACKET PRODUCED BY THIS METHOD

(71) Applicant: DW Lingual System GmbH, Bad Essen (DE)

(72) Inventor: Dirk Wiechmann, Bad Essen (DE)

(73) Assignee: DW Lingual System GmbH, Bad Essen (DE)

( * ) Notice: Subject to any disclaimer, the term of this patent is extended or adjusted under 35 U.S.C. 154(b) by 409 days.

(21) Appl. No.: 14/892,479

(22) PCT Filed: May 14, 2014

(86) PCT No.: PCT/EP2014/059897
§ 371 (c)(1),
(2) Date: Dec. 9, 2015

(87) PCT Pub. No.: WO2014/187715
PCT Pub. Date: Nov. 27, 2014

(65) Prior Publication Data
US 2016/0113737 A1    Apr. 28, 2016

(30) Foreign Application Priority Data

May 24, 2013  (DE) .................. 10 2013 209 735

(51) Int. Cl.
*A61C 7/00* (2006.01)
*A61C 7/14* (2006.01)
*A61C 7/16* (2006.01)

(52) U.S. Cl.
CPC ................ *A61C 7/002* (2013.01); *A61C 7/14* (2013.01); *A61C 7/145* (2013.01); *A61C 7/146* (2013.01); *A61C 7/16* (2013.01)

(58) Field of Classification Search
CPC ........... A61C 7/146; A61C 7/145; A61C 7/16; A61C 7/14; A61C 9/004; A61C 7/002;
(Continued)

(56) References Cited

U.S. PATENT DOCUMENTS

| 6,015,289 A | 1/2000 | Andreiko et al. |
| 2003/0152884 A1 | 8/2003 | Wiechmann et al. |

(Continued)

FOREIGN PATENT DOCUMENTS

| AT | 391614 B | 11/1990 |
| DE | 19540755 A1 | 5/1997 |
| WO | 2001085047 A2 | 11/2001 |

*Primary Examiner* — Matthew P Travers
(74) *Attorney, Agent, or Firm* — Steven P. Fallon; Greer, Burns & Crain, Ltd.

(57) ABSTRACT

A process to manufacture a patient-specific replacement bracket includes providing a 3D representation of the supramaxilla or submaxilla of a patient in the target set-up with a reference plane in a computer. A request to manufacture a replacement bracket is received. A sector of the 3D representation is defined and contains at least a section of the tooth for which the replacement bracket is to be manufactured. A marking is generated for the slot plane in the sector. A physical model of the sector with the marking is created. A bracket element containing the slot is provided. The bracket element is aligned to the slot plane. An individualized pad is assigned to the bracket element, whereby the replacement bracket is manufactured.

31 Claims, 7 Drawing Sheets

(58) Field of Classification Search
CPC .... Y10T 29/49567–29/49568; Y10T 29/4973;
Y10T 29/49746
See application file for complete search history.

(56) References Cited

U.S. PATENT DOCUMENTS

| | | | |
|---|---|---|---|
| 2006/0275736 A1* | 12/2006 | Wen | A61C 9/00 433/213 |
| 2009/0017410 A1 | 1/2009 | Raby et al. | |
| 2010/0216085 A1* | 8/2010 | Kopelman | A61C 7/146 433/24 |
| 2018/0104022 A1* | 4/2018 | Cheang | G06T 19/20 |

* cited by examiner

METHOD FOR PRODUCING A PATIENT-SPECIFIC REPLACEMENT BRACKET FOR AN ORTHODONTIC TREATMENT, AND BRACKET PRODUCED BY THIS METHOD

The invention relates to a process for the manufacture of a patient-specific replacement bracket for orthodontic treatment and to a bracket manufactured according to the process.

For orthodontic treatment of patients with fixed-brace, brackets are bonded to the teeth of the patient to be treated and connected together by an orthodontic wire. The brackets have a pad for connection with the tooth and a bracket body with a slot that receives the wire.

Preferably, brackets are used for orthodontic treatment which have an individualized pad, i.e. the pad of the bracket has an adhesive surface for connection with the tooth which is adapted to the respective tooth, so that the bracket can be placed in a certain position in a form-fit on the tooth.

During the treatment it may happen that a bracket detaches from its tooth and it must therefore be replaced.

In such a case, typically, a completely individualized replacement bracket is manufactured by means of an existing target set-up of gypsum. In practice the procedure is especially complicated in that the already existing target set-up usually must be sent first to a technical workshop and there the replacement bracket must be manufactured then and sent back.

A disadvantage in the manufacture of a completely individualized replacement bracket is that the process is complex, especially gypsum models of set-ups need to be consigned.

An object of the present invention is therefore to provide a simpler and more cost-effective process for the manufacture of a completely individualized replacement bracket.

According to the invention, the object is achieved by a process with the features of claim 1, which leads to a corresponding bracket according to its independent claim.

Advantageously, Step 1a) comprises: 2a) Creating a patient-specific target set-up of the supramaxilla or submaxilla of a patient, 2b) determining a slot plane of a bracket to be arranged on the teeth of the supramaxilla or submaxilla to be treated, 2c) disposing of brackets on the teeth of the supramaxilla or submaxilla to be treated, 2d) determining the reference plane in the target set-up relative to the slot plane, 2e) removing the brackets from the target set-up, and 2f) electronically storing the target set-up, including the reference plane.

Preferably, Step 2a) is carried out by means of a gypsum model or by means of a virtual model of the supramaxilla or submaxilla.

Step 2d) may be carried out prior to Step 2c).

In Step 2f) electronically storing is effected by scanning a physical target set-up or by storing a digital target set-up.

In Step 1f) a lingual or buccal bracket element may be provided as a bracket element in order to manufacture a lingual bracket or a buccal bracket as a replacement bracket.

The reference plane in Step 1a) may be displayed continuously, for example by a line, or intermittently, for example dash-dotted, on selected teeth.

The reference plane in Step 1a) may be defined the same for all teeth, for example, from 18 to 28, or be selected for a selected region, for example, from 13 to 23, and for the remaining regions a displacement relative thereto, for example, lowering or elevating of the reference plane, may be defined.

The reference plane may be defined at a fixed distance, for example, 3 to 6 cm from the slot plane. or individually, in particular the reference plane and slot plane are identical.

The relevant sector to be defined in Step 1c) may comprise at least a section of the tooth and preferably the tooth, particularly with an additional gingival section, optionally at least an additional section of the mesially and/or distally adjacent tooth, preferably the whole tooth, in particular each with an additional gingival section.

The marking may be realized as a 2D line or as a 3D body, in particular as a retaining section for the tooth.

In the case of a 2D line the marking may be arranged on the upper or lower edge of a slot in the slot plane, or in the case of a 3D body at the level of the slot plane, wherein in the latter case, the 3D body in occlusal-gingival direction preferably has a thickness that corresponds to the level of the slots of the brackets in this direction.

The retaining section for buccal brackets is arranged preferably lingually and for lingual brackets preferably buccally.

The retaining section in Step 1g) is preferably connected with a technician's holder.

The creating of the model in Step 1e) may be effected by printing the sector with a 3D printer or by means of a CNC machine or a rapid prototyping machine.

The sector in Step 1c) may be defined manually or automatically, for examples, by software.

In Step 1h) the bracket body may be connected with an individualized pad or the standard bracket may be provided with an individualized pad, for example, by filling a gap between the tooth and the pad of the standard bracket with a plastic material and curing the same.

In Step 1d) a 2D marking may be generated, for example, in the form of a line or dots, whereby the slot level and the angulation of the corresponding bracket are defined.

In Step 1d) a 3D marking may be generated, for example, in the form of a pin, whereby the slot level, the angulation and the torque of the corresponding bracket are defined.

In Step 1d) a 3D marking may be generated with the help of at least one bracket constraint, for example, in the form of a pin, whereby the slot level, the angulation, the torque and the rotation of the corresponding brackets are defined.

As the bracket constraint, a perpendicular to a bracket center that extends perpendicularly to the slot, or the position and the profile of the slot can be used, wherein the constraint preferably is additionally stored in the 3D presentation of the supramaxilla or submaxilla provided in Step 1a).

As marking, a pin-shaped retaining section is preferably generated having a lateral surface that is arranged at the level of the upper or lower edge of the slot of the corresponding bracket.

Further features, details, and advantages of the invention become apparent from the claims, and the following description of preferred embodiments and on the basis of the drawing. Figures show the following:

FIG. 1 a buccal lateral view of a target set-up of a submaxilla from the right in the gypsum model, FIG. 2 two lateral views of a tooth section with a retaining element, FIG. 3 a level adjustment between a tooth receptacle for the tooth section of FIG. 2 and a holder for the bracket element having a slot, FIG. 4 a lateral view of the tooth receptacle with inserted tooth section and a holder with bracket placed on, FIG. 5 a perspective view of FIG. 4, FIG. 6 various views in which the bracket is bonded to the tooth section, and FIG. 7 a perspective view of the tooth section with the bracket of FIG. 6, but without a retaining element.

The process is now illustrated by means of the manufacture of a replacement bracket for any tooth of a jaw by taking the example of the submaxilla. To manufacture a replacement bracket according to the invention, one proceeds as follows: A gypsum model of the submaxilla of a patient is created, which is to be treated by orthodontic means. The gypsum model is sawn resulting in the teeth being separated. Subsequently, the teeth are arranged in a target set-up 11, cf. FIG. 1, which is supposed to display the desired outcome at the end of treatment.

Figure 1:
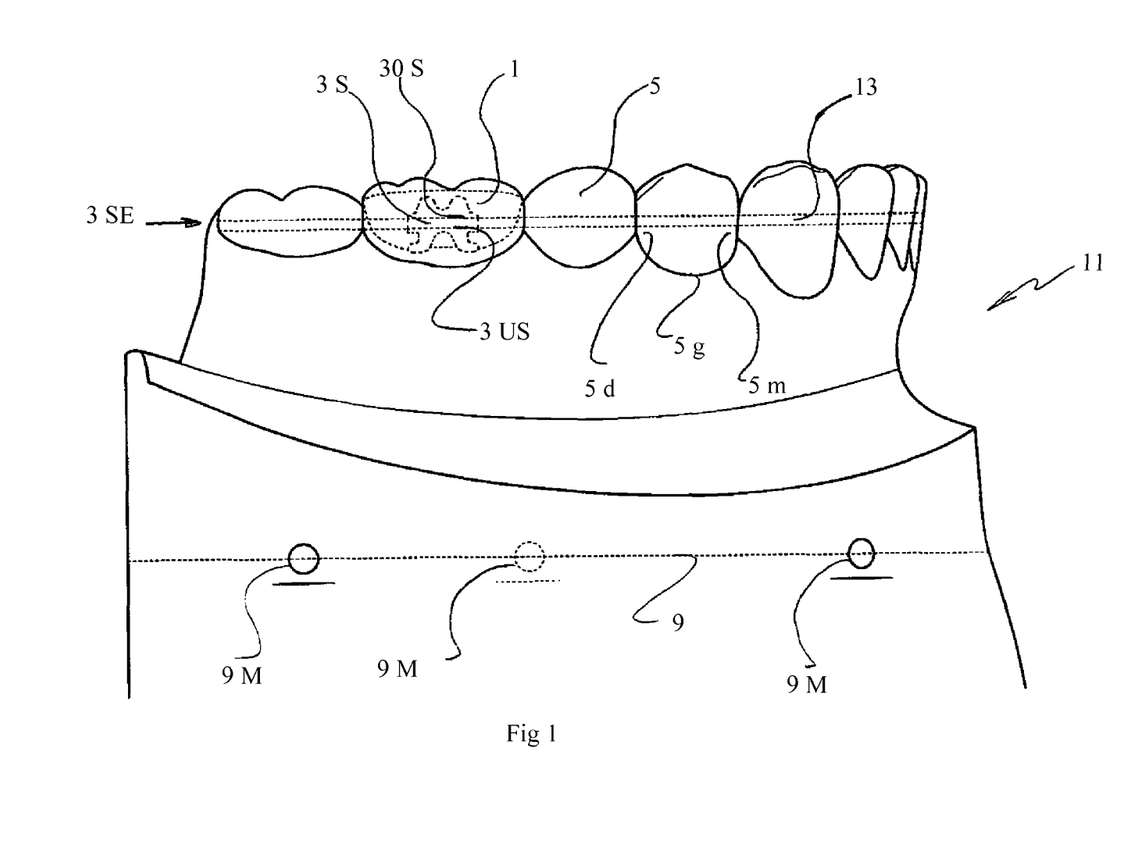

Then, brackets 1 are bonded to the teeth 5 to be treated. In the target set-up 11 of FIG. 1, lingual brackets 1 are bonded to the teeth 5 to be treated; only one bracket 1 on tooth is depicted in FIG. 1 as representative in dashed lines. For illustration, in the slots 3S of the brackets 1, an orthodontic wire 13 is guided, also shown only in broken lines in order to exert via the slots 3S and the brackets 1 a force on the teeth 5, in order to move the respective teeth 5 to a desired position. At the end of the orthodontic treatment all the slots 3S of the brackets 1 shall essentially lie in one plane, the so-called slot plane 3SE, as shown in FIG. 1.

Up to this point, the process according to the invention corresponds to some conventional planning processes for an orthodontic treatment: A target set-up 11 is made of gypsum and brackets 1 are bonded on the teeth 5, wherein said slots 3S of the brackets lie in one plane 3SE.

At a defined distance from the slot plane 3SE, for example, the upper edge 3OS or the lower edge 3US of the slots 3S of the brackets 1, a reference plane 9 is now defined. The reference plane 9 is shown in FIG. 1 by dashed lines. It is presently defined by three reference plane markings 9M in the form of circles on the gypsum model, of which the respective centers define the reference plane 9. Of the three reference plane markings 9M, one is shown dashed because it is located on the opposite (hidden left) side of the gypsum model. The reference plane 9 has a fixed distance from the lower edge 3US of the slots 3S of the brackets 1, for example, a distance of an interval from 1 to 10 cm, presently 3 cm.

As soon as the reference plane 9 is defined and marked on the target set-up 11, then the brackets 1 are removed from the target set-up 11, resulting in the target set-up 11 of FIG. 1 without the bracket 1 illustrated in dashed lines and the wire 13 illustrated in dashed lines.

The thus manufactured target set-up 11 will now be scanned using a scanner and the digital computer model of the target set-up 11 is stored in a computer. A model of the target set-up 11 is thus available in the computer, which also contains the reference plane 9. Because the computer model contains the reference plane 9, and the relation between the slot plane 3S and the reference plane 9 is known, the slot plane 3S is thus also defined for the computer model.

If now the request arrives to manufacture a replacement bracket for a particular tooth, the procedure is as described in the following.

The above-mentioned computer model of the target set-up 11 is loaded into the computer. The tooth 5, for which the replacement bracket is to be fabricated, is selected in the model and cut out by hand from the rest of the model, so that only the computer model of the respective tooth 5 is present for subsequent processing.

Using the reference plane 9, which is still available in the computer model, a marking for the lower edge 3US of the slot plane 3SE of the slot 3S of the bracket 1 corresponding to the respective tooth 5 is added to tooth 5. To be able to handle the physical model of the tooth in the following working steps, a retaining section of the tooth is added to the computer model, shown herein exemplarily in the form of a pin. For simplification, the retaining section is added to the computer model of the tooth such that an edge of the retaining section is arranged at the level of the lower edge 3US of the slot 3S. The computer model of the tooth now arises from the representation of FIG. 2.

Figure 2:
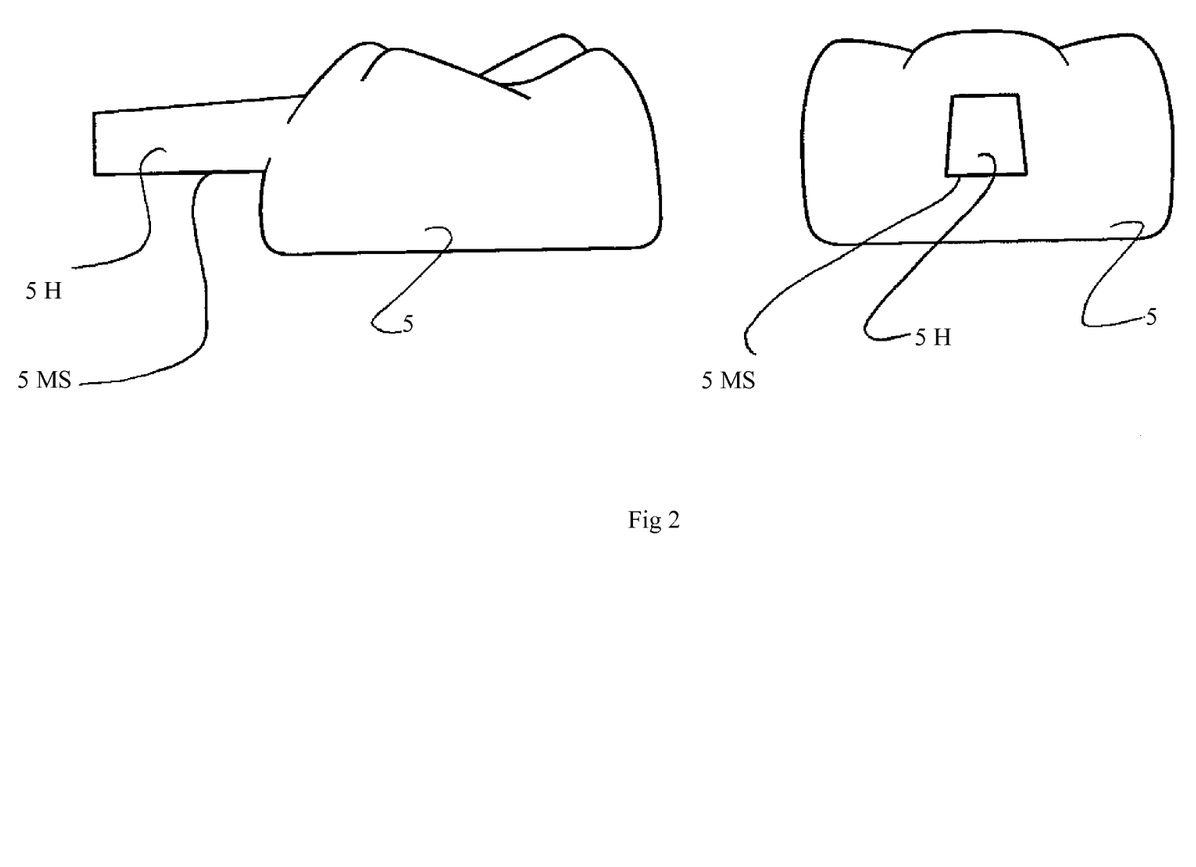

FIG. 2 shows two lateral views of a 3D model of the tooth 5, for which a replacement bracket shall be manufactured. From the tooth 5, only that section can be seen, which lies above the gingival edge, i.e., the normally visible part of the patient's tooth 5. A retaining section 5H in the form of a pin was added to the tooth 5 as retainer. The retaining section 5H has as cross-section substantially in the shape of a rectangle, wherein in FIG. 2 the upper lateral edge of the rectangle is slightly shortened compared to the lower lateral edge. The retaining section 5H is arranged on the model of the tooth 5 such that the lower lateral edge in FIG. 2 is a marking 5MS for the slot plane, i.e., this edge is arranged at the level of the lower edge 3US of the slot 3S of the corresponding bracket 1.

A model of the tooth 5, for which a replacement bracket shall be manufactured, thus is available in the computer. The model was extended by the retaining section 5H, which has the form of a pin and one edge of which is arranged at the level of the lower edge 3US of the slot 3S of the corresponding bracket 1.

The computer model of FIG. 2 created in this way is created in the next step as a physical model, for example, printed, or produced out of plastic by means of a 3D printer. Then, a plastic model of the tooth 5 is available, which has a level mark for the lower edge 3US of the slot 3S and has a retaining section 5H for holding the physical model.

Figure 3:
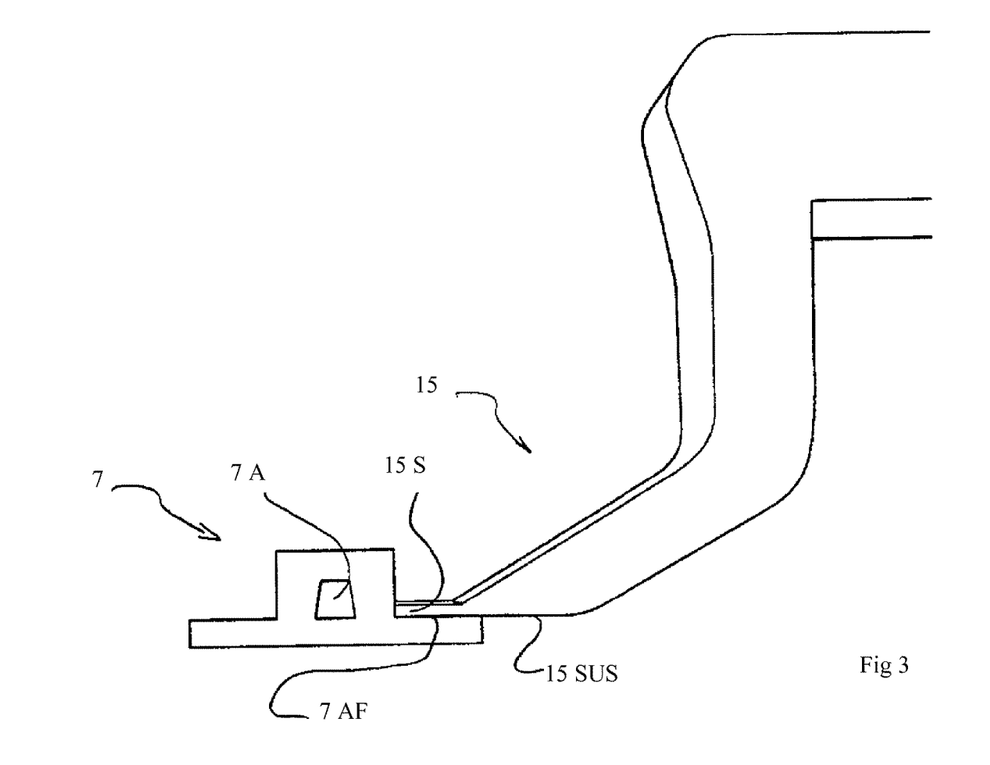

FIG. 3 shows the front view of a retaining section seat 7 of a technician's holder, which is adapted for receiving the retaining section 5H of the printed tooth 5, and the lateral view of a slot receptacle 15 of another technician's holder for receiving a slot 3S.

The slot receptacle 15 has, in the view of FIG. 3 in a vertical direction at the free end, the thickness of a slot-filling orthodontic wire. The free end simulates in this way a slot-filling orthodontic wire, i.e. it forms a wire simulator 15S. A slot 3S of a bracket can thus be pushed without play onto this wire simulator 15S, as described below. After level adjustment as described below the underside 15SUS of the wire simulator 15S lies on the same level as the lower edge 3US of a slot 3S of the bracket 1 corresponding to the tooth 5, as shown in FIG. 3.

The retaining section seat 7 centrally has a recess 7A which is dimensioned such that the retaining section 5H of the printed tooth 5 can be inserted therein in a form-fit manner. As described above, the lower edge of the recess 7A in FIG. 3 is at the level of the lower edge 3US of the slot 3 of the bracket 1 corresponding to the tooth 5. The support surface 7AF of the retaining section seat 7 on which the underside 15SUS rests is on the same level as the underside of the recess 7A.

The slot receptacle 15 on the one technician's holder and the retaining section seat 7 is on the other technician's holder each have edges that are at the level of the lower edge 3US of the slot 3S of the bracket 1 belonging to the tooth 5. To relate these levels to the same zero point, these levels are adjusted to each other, as shown in FIG. 3. The underside 15SUS is placed on the depicted support surface 7AF of the retaining section seat 7 and thus the reciprocal zero points of the slot receptacle 15 and of the retaining section seat 7 are adjusted to each other, whereby the level adjustment is completed.

Figure 4:
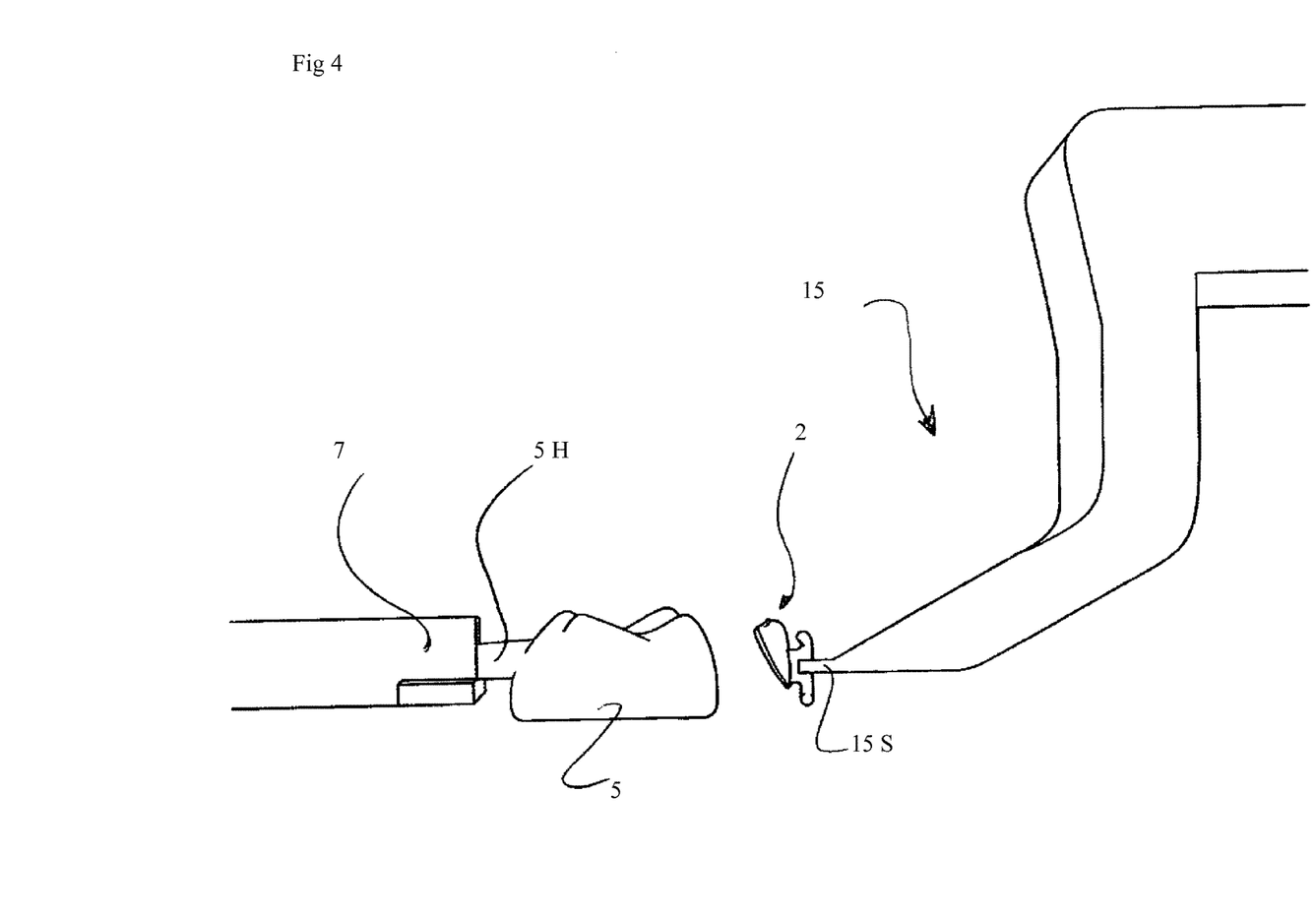

In a next process step, the printed tooth 5 with its retaining section 5H is inserted into the recess 7A of the retaining section seat 7 and a standard bracket 2 is placed on the wire simulator 15S of the slot receptacle 15, as shown in FIG. 4. As also seen from FIG. 4, the printed tooth 5 and the standard bracket 2 are each brought together to properly place the standard bracket 2 onto the printed tooth 5.

Figure 5:
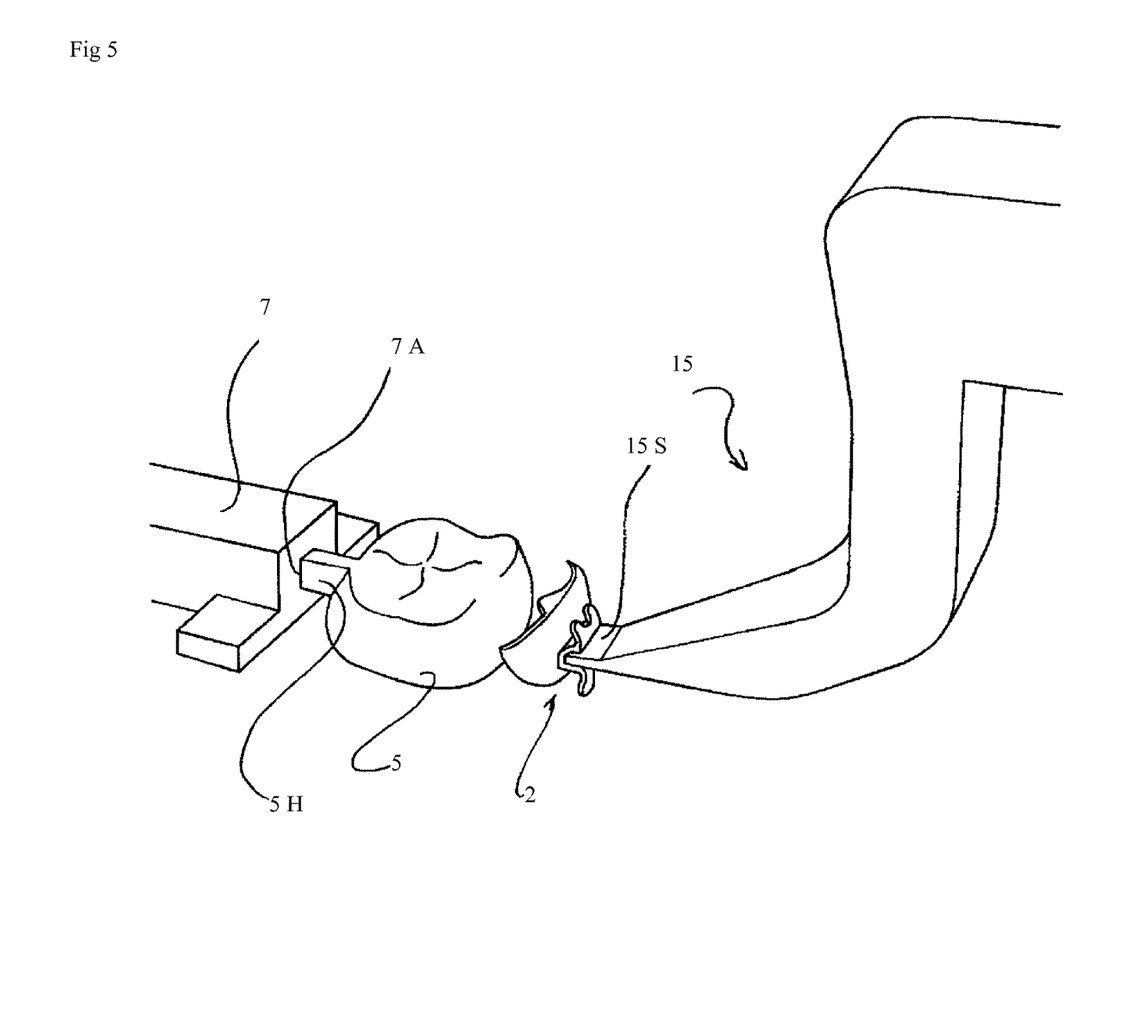

FIG. 5 shows a perspective view of the arrangement shown in FIG. 4.

As soon as the standard bracket 2 is properly positioned relative to the printed tooth 5, then a gap between the pad of the standard bracket 2 and the printed tooth 5 is filled and cured with a plastic material or an adhesive, to form a patient-specific pad for the standard bracket 2.

Figure 6:
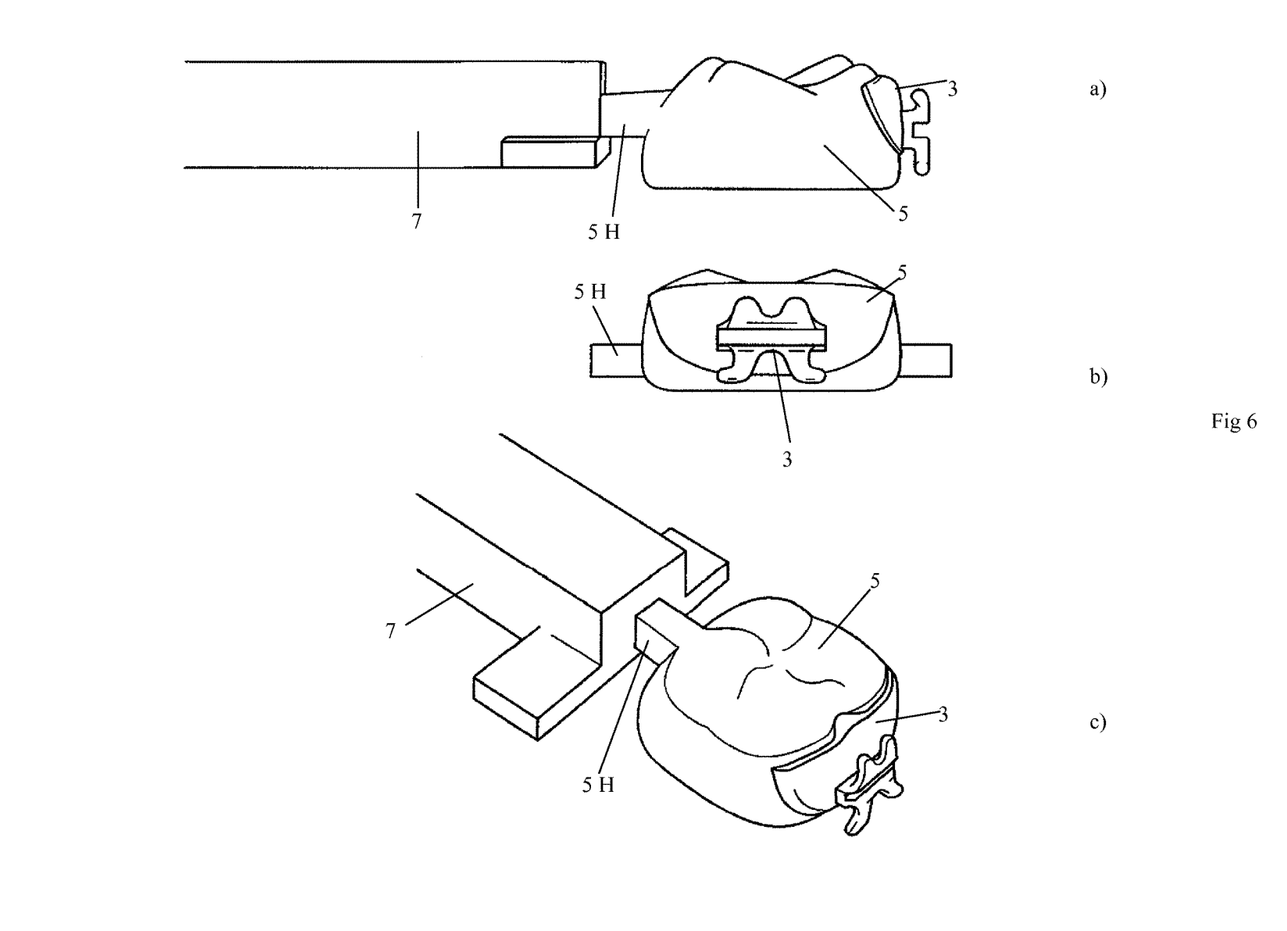

When curing has occurred, the technician's holder with the slot receptacle can be removed, resulting in the configuration shown in FIG. 6. FIG. 6 shows various views of the standard bracket 2 bonded onto the printed tooth 5, which now forms the replacement bracket 3.

Figure 7:
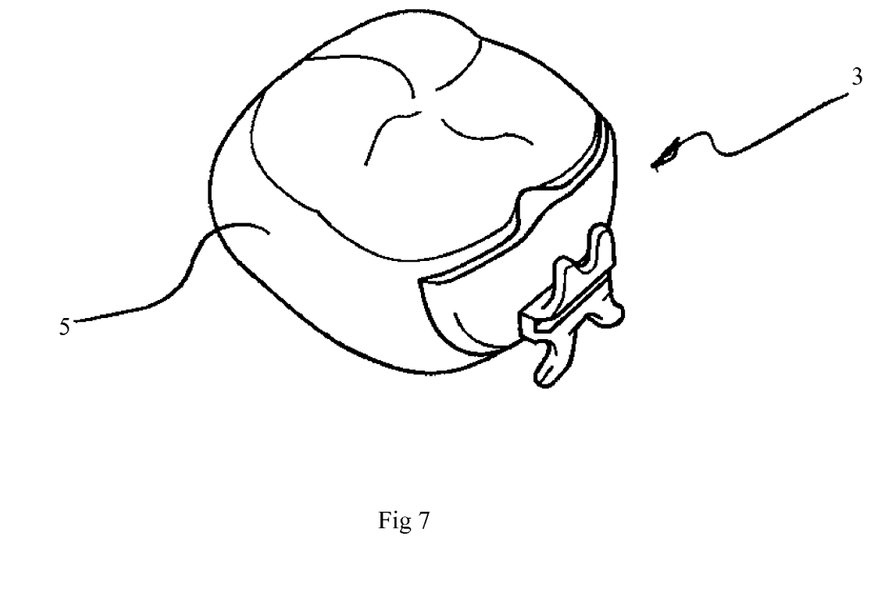

Subsequently, the retaining section 5H is pulled out of the recess 7A and the retaining section 5H is removed from the printed tooth 5, for example, by grinding, whereby the arrangement of FIG. 7 is obtained. This arrangement can now be sent to the purchaser of the replacement bracket.

When the arrangement of FIG. 7 reaches the purchaser of the replacement bracket, then he can detach the standard bracket 2 with the plastic material on the pad's side from the printed tooth 5 and thus obtains the replacement bracket 3. The replacement bracket 3 thus comprises the standard bracket 2 and the individualized pad, which is formed of the cured plastic material.

The replacement bracket 3 can be bonded by the individualized pad form fittingly to the tooth 5 of the patient.

A lingual bracket was manufactured in the above-mentioned process for the manufacture of a replacement bracket. However, the process can be used in the same manner to manufacture buccal brackets.

The reference plane 9 was depicted in the above-described process as a plane, which is valid for all of the teeth 5 of a jaw of a patient. However, it may be necessary to define the reference plane 9 only for selected regions of a jaw, i.e. subdivide it into intervals. In some cases, it proves to be necessary to lower the slot plane, and thus the reference plane on the left and/or right lateral teeth area for orthodontic reasons. In such a case, the reference plane from 47 to 33 can lie at one level, and for the range from 34 to 37 it can lie at a different level, for example, be lowered by 1 mm relative to the other. In another case, a reference plane can be defined from 33 to 43, and in the region from 34 to 37 a lowering by 0.5 mm and in the region from 44 to 47 a lowering by 1 mm can be defined. In such cases, it may be sufficient to note down only the lowering or raising in the affected tooth areas and the affected tooth areas and not to draw the lowering or elevation in the model. In this way, the reference plane receives variable levels in defined sections by adjusting the slot plane in these sections.

The reference plane 9 can be arranged on the same side as the brackets 1, i.e. drawn in on the buccal side in case of buccal brackets and on the lingual side in case of lingual brackets. Alternatively, it is also possible to draw in the reference plane on the other respective side. For example, it is possible in case if buccal brackets to draw in the reference plane 9 on the lingual side, in particular on the lingual side of some selected or all of the teeth. In this way, the reference plane 9 can be drawn in for each tooth individually, and in a small spatial distance from the slot 3S of the corresponding bracket 1. Thus, it is for example possible to use the lower edge 3US of a slot 3S of a bracket 1 as a reference plane 9 for the corresponding tooth 5.

In the above-described process of manufacturing a replacement bracket, the target set-up was prepared from gypsum. Alternatively, it is possible to create the target set-up in a computer by means of software. Also the other steps, such as, for example, the arrangement of brackets on the teeth, the definition of the slot plane and definition of the reference plane can be executed directly in the software. The virtual set-up resulting thereby can be stored with the brackets, the orthodontic wire, the slot plane and the reference plane, or even only with parts of it, for example only with the slot plane and the reference plane. If then a request for manufacturing a replacement bracket comes in, the desired section of the tooth can be manufactured directly from the model.

To manufacture the replacement bracket for the tooth 5, in the process described above, the part of the tooth 5 visible in the patient was cut out by hand from the rest of the computer model of the target set-up 11. For the manufacture of the replacement bracket, however, it may be sufficient to select a small section of the tooth, for example, to print only the buccal half of the tooth without the lingual half of the tooth. However, it may also be necessary to select a larger section, for example, to add a gingival section 5g, see FIG. 1, or to add mesial and/or distal sections 5m, 5d of adjacent teeth 5, see FIG. 1. Defining the relevant section may be done manually, as described earlier. However, it is also possible to define the relevant section by means of software. Thus, for example, with the aid of an edge-finder algorithm, the tooth 5 as shown in FIG. 2 can always be identified automatically and cut out from the rest of the computer model.

The above-described process for manufacturing a replacement bracket generates a patient-specific pad for a standard bracket. With the standard bracket, pad and bracket body are one unit and the patient-specific pad is generated to manufacture the patient-specific replacement bracket. However, there are also other methods of manufacture of patient-specific brackets, where, for example, first a pad with a patient-specific bonding surface is manufactured, and then the pad manufactured in this manner is united with a bracket body to form a bracket. Such a process of manufacture is, for example, disclosed in DE102011003892. The process of manufacture according to the invention is also suitable for this type of process of manufacture. For this purpose, one may proceed as described above, and in FIGS. 4 and 5, the bracket body must solely be placed on the slot receptacle 15 and the patient—specific pad onto the printed tooth 5 to subsequently fix the bracket body on the individualized pad, for example by laser welding, to manufacture the patient-specific replacement bracket.

In the above described process of manufacture of a replacement bracket, a retaining section 5H was added to the computer model of the tooth 5 as a marking for the slot plane. In doing so, only the level of the retaining section 5H was defined such that its lower edge is at the level of the lower edge 3US of the slot 3S of the bracket. Where the retaining section 5H is located along the tooth circumference (at the same level), is at present irrelevant, so that the retaining section 5H, for example, can be arranged mesially, lingually or distally for a buccal bracket.

For various kinds of markings of the slot plane on the tooth in the computer model, various other parameters of the treatment of the tooth can be specified:

If the slot plane is defined on the tooth by means of a 2D marking, for example, by a line, strip or a series of points, then by this marking only the slot level and angulation, i.e., the tilt in mesial-distal direction, of the bracket are defined.

If the slot plane is defined on the tooth by means of a 3D marking, such as, for example, by the pin-shaped retaining section 5H according to FIG. 2, then the slot level, the angulation and the torque, i.e. the tilt in lingual-buccal direction, of the bracket are defined.

If the slot plane is uniquely defined on the tooth by means of a 3D marking at a predetermined position, i.e., without a free degree of freedom, for example, such that the retaining section 5H of FIG. 2 is printed at the same level along the tooth circumference at a particular circumferential location, then slot level, angulation, torque and rotation, i.e., the rotation about the longitudinal axis of tooth, of the bracket are defined.

In order to realise the latter variant, for example, one can proceed as follows: In the computer model additional information, i.e. a bracket constraint is stored for each bracket, which makes its location on the tooth definite. As additional information, for example, a line passing through the bracket center and perpendicularly to a surface of the bracket can be used. As additional information, also the slot of the bracket, i.e. its location or arrangement in space can be stored with it.

In practice, one can proceed as follows: The target set-up 11 illustrated in FIG. 1 is stored first with brackets and then without brackets. Based on the computer model without brackets, a 3D marking is then added to the tooth 5 in the process according to the invention, for example, a retaining section 5H shown in FIG. 2. The location of the retaining section 5H along the tooth circumference is then defined using the computer model with brackets: The model with brackets is loaded over the other model and the retaining section 5H, for example, is displaced so long along the tooth circumference until it is exactly opposite the bracket from the target set-up 11, i.e. that the longitudinal axis of the retaining section 5H exactly extends perpendicularly to the longitudinal axis of the slot and passes through the slot center. Then, in the later step, which corresponds to arranging the standard bracket 2 as shown in FIGS. 4 and 5, the bracket can be aligned to the retaining section 5H until the standard bracket 2 is exactly opposite the retaining section 5H. The standard bracket 2 then has exactly the location as the bracket 1 during the initial scan of the models with and without brackets.

LIST OF REFERENCE NUMBERS 1 bracket
2 standard bracket
3 replacement bracket
3S slot
3OS upper edge of slot
3US lower edge of slot
3SE slot plane
5 tooth
5d distal section
5g gingival section
5H retaining section for tooth
5m mesial section
5MS marking for the slot plane
7 retaining section seat of a technician's holder for the retaining section 5H
7A recess of the retaining section seat
7AF support surface
9 reference plane
9M reference plane marking
11 target set-up of the submaxilla of a patient
13 orthodontic wire
15 slot receptacle of a technician's holder for receiving a slot 3S
15S wire simulator
15SUS underside of the wire simulator

The invention claimed is:

1. A process of manufacture of a patient-specific replacement bracket comprising the following steps of:
    a) providing a 3D representation of the supramaxilla or submaxilla of a patient in a target set-up with a reference plane in a computer;
    b) receiving a request to manufacture a replacement bracket for a tooth of the supramaxilla or submaxilla;
    c) defining a sector of the 3D representation of the supramaxilla or submaxilla which contains at least a section of the tooth for which the replacement bracket is to be manufactured;
    d) generating a marking for a slot plane in the sector by means of the reference plane;
    e) creating a physical model of the sector with the marking;
    f) providing a bracket element containing a slot;
    g) aligning said bracket element to the slot plane; and
    h) assigning an individualized pad to the bracket element, whereby the replacement bracket is manufactured.

2. The process according to claim 1 wherein Step 1a) comprises:
    a) creating a patient-specific target set-up of the supramaxilla or submaxilla of a patient;
    b) determining a slot plane of the bracket to be arranged on teeth of the supramaxilla or submaxilla to be treated,
    c) arranging of brackets on the teeth to be treated of the supramaxilla or submaxilla;
    d) determining the reference plane in the target set-up relative to the slot plane;
    e) removing the brackets from the target set-up; and electronically storing the target set-up, including the reference plane.

3. The process according to claim 2, wherein Step 2a) is carried out by means of a gypsum model or by means of a virtual model of the supramaxilla or submaxilla.

4. The process according to claim 2, wherein Step 2d) is carried out prior to step 2c).

5. The process according to claim 2, wherein the electronically storing in Step 2f) is effected by scanning a physical target set-up or by storing a digital target set-up.

6. The process according to claim 1, wherein in Step 1f) a lingual or buccal bracket element is provided as a bracket element in order to manufacture a lingual or buccal bracket as a replacement bracket.

7. The process according to claim 1, wherein the reference plane in Step 1a) is displayed continuously on selected teeth.

8. The process according to claim 7, wherein the reference plane is displayed by a line.

9. The process according to claim 7, wherein the reference plane is displayed by dash dots.

10. The process according to claim 1, wherein the reference plane in Step 1a) is defined the same for all teeth or is defined for a selected region and for the remaining regions a displacement relative thereto.

11. The process according to claim 10, wherein the displacement is a lowering of the reference plane.

12. The process according to claim 10, wherein the displacement is a raising of the reference plane.

13. The process according to claim 1, wherein the reference plane is defined at a fixed distance, for example from the slot plane, or is defined individually.

14. The process according to claim 13, wherein the fixed distance is from 3 to 6 cm.

15. The process according to claim 13, wherein the reference plane is identical with the slot plane.

16. The process according to claim 1, wherein the marking is realized as a 2D line or as a 3D body.

17. The process according to claim 16, wherein in the case of a 2D line the marking is arranged on an upper or lower edge of a slot in the slot plane, or in the case of a 3D body is arranged at the level of the slot plane, wherein in the latter case the 3D body in occlusal-gingival direction has a thickness that corresponds to the level of the slot of the bracket in this direction.

18. The process according to claim 16, wherein the marking realized as a 3D body is a retaining section for the tooth.

19. The process according to claim 1, wherein the marking is realized as a retaining section arranged lingually for buccal brackets and buccally for lingual brackets.

20. The process according to claim 19, wherein the retaining section is connected to a technician's holder in Step 1g).

21. The process according to claim 1, wherein creating the model in Step 1c) is effected by printing the sector with a 3D printer, or by means of a CNC machine or a rapid prototyping machine.

22. The process according to claim 1, wherein the sector in Step 1c) is defined manually or automatically.

23. The process according to claim 1, wherein in Step 1h) a bracket body is connected with an individualized pad, or a standard bracket is provided with an individualized pad, by filling a gap between the sector and a pad of the standard bracket with a plastic material and curing the same.

24. The process according to claim 1, wherein in Step 1d) a 2D marking is generated, whereby the slot level and angulation of the corresponding bracket are defined.

25. The process according to claim 1, wherein in Step 1d) a 3D marking is generated, whereby the slot level, the angulation and the torque of the corresponding bracket are defined.

26. The process according to claim 1, wherein in Step 1d) a 3D marking is generated with the help of at least one bracket constraint, whereby the slot level, the angulation, the torque and the rotation of the corresponding bracket are defined.

27. The process according to claim 26, wherein a perpendicular to a bracket center that extends perpendicularly to the slot is used as the bracket constraint, or the position and the profile of the slot are used, wherein the constraint is additionally stored in the 3D representation of the supramaxilla or submaxilla provided in Step 1a).

28. The process according to claim 27, wherein as the marking a pin-shaped retaining section is generated having a lateral surface that is arranged at the level of an upper or lower edge of the slot of the corresponding bracket.

29. The process according to claim 26, wherein the bracket constraint is in the form of a pin.

30. The process according to claim 1, wherein the bracket element containing the slot is a bracket body.

31. The process according to claim 1, wherein the bracket element containing the slot is a standard bracket.

* * * * *